(12) United States Patent
Cane'

(10) Patent No.: US 9,463,271 B2
(45) Date of Patent: Oct. 11, 2016

(54) PORTABLE PUMP FOR INFUSING LIQUID SUBSTANCES INTO THE BODY OF A LIVING BEING AND RESERVOIR FOR USE IN SAID PUMP

(71) Applicant: Cane' S.p.A., Rivoli (IT)

(72) Inventor: Mario Cane', Collegno (IT)

(73) Assignee: Cane' S.p.A., Rivoli, (TO) (IT)

( * ) Notice: Subject to any disclaimer, the term of this patent is extended or adjusted under 35 U.S.C. 154(b) by 297 days.

(21) Appl. No.: 14/341,937

(22) Filed: Jul. 28, 2014

(65) Prior Publication Data

US 2015/0038906 A1 Feb. 5, 2015

(30) Foreign Application Priority Data

Aug. 2, 2013 (IT) .............. TO2013A0661

(51) Int. Cl.
| | |
|---|---|
| *A61M 37/00* | (2006.01) |
| *A61M 1/00* | (2006.01) |
| *A61M 5/14* | (2006.01) |
| *A61M 5/145* | (2006.01) |
| A61M 5/142 | (2006.01) |
| A61M 5/24 | (2006.01) |

(52) U.S. Cl.
CPC ........... *A61M 5/1413* (2013.01); *A61M 5/145* (2013.01); *A61M 5/14244* (2013.01); *A61M 5/14566* (2013.01); *A61M 2005/14264* (2013.01); *A61M 2005/14268* (2013.01); *A61M 2005/14506* (2013.01); *A61M 2005/2488* (2013.01); *A61M 2205/123* (2013.01); *A61M 2205/33* (2013.01)

(58) Field of Classification Search
CPC .......... A61M 2005/14506; A61M 2005/2488; A61M 2205/123; A61M 2205/33; A61M 5/1413; A61M 5/14244; A61M 5/145; A61M 5/14566

See application file for complete search history.

(56) References Cited

U.S. PATENT DOCUMENTS

| | | |
|---|---|---|
| 2,702,547 A | 2/1955 | Glass |
| 4,662,872 A | 5/1987 | Cane' |
| 5,938,640 A | 8/1999 | Maget et al. |
| 6,447,487 B1 | 9/2002 | Cane' |
| 6,585,695 B1 | 7/2003 | Adair et al. |
| D565,176 S | 3/2008 | Cane' |

(Continued)

FOREIGN PATENT DOCUMENTS

WO 2008/077914 A2 7/2008

OTHER PUBLICATIONS

Search Report and Written Opinion issued for counterpart Italian Patent Application No. TO2013A000661 dated Apr. 2014.

*Primary Examiner* — Rebecca E Eisenberg
(74) *Attorney, Agent, or Firm* — Howson & Howson, LLP

(57) ABSTRACT

A portable pump for infusing liquid substances into a body is provided. The pump has a casing and electromechanical members for converting rotary motion of a motor shaft into linear sliding motion of a pusher for causing movement of a plunger slideable within an interchangeable reservoir in which the substance to be infused is contained in a housing. The housing communicates through an opening formed in a casing wall through which the reservoir can be inserted into and removed from the housing and from which an appendix of the reservoir protrudes for the exit of the substance. The housing has a distal portion with mechanical means for reversible engagement of the reservoir end opposite to the appendix and a proximal portion provided with an annular sealing gasket which surrounds the reservoir and forms a seal between the reservoir and casing wall.

10 Claims, 4 Drawing Sheets

(56) References Cited

U.S. PATENT DOCUMENTS

| | | |
|---|---|---|
| D659,234 S | 5/2012 | Cane' |
| 2004/0092873 A1* | 5/2004 | Moberg ............... A61M 5/1456 604/131 |
| 2005/0177108 A1 | 8/2005 | Paul et al. |
| 2007/0078393 A1 | 4/2007 | Lynch et al. |
| 2007/0093750 A1 | 4/2007 | Jan et al. |
| 2007/0191770 A1* | 8/2007 | Moberg ............ A61M 5/14566 604/131 |
| 2009/0126463 A1 | 5/2009 | Friedli et al. |
| 2010/0106091 A1 | 4/2010 | Wright et al. |
| 2011/0144586 A1 | 6/2011 | Michaud et al. |
| 2011/0202005 A1 | 8/2011 | Yodfat et al. |
| 2012/0030610 A1 | 2/2012 | DiPerna et al. |
| 2012/0143133 A1 | 6/2012 | Cane' |
| 2013/0303990 A1* | 11/2013 | Lynch ............... A61M 5/14244 604/152 |
| 2013/0338635 A1* | 12/2013 | O'Connor ......... A61M 5/16859 604/506 |

* cited by examiner

PORTABLE PUMP FOR INFUSING LIQUID SUBSTANCES INTO THE BODY OF A LIVING BEING AND RESERVOIR FOR USE IN SAID PUMP

BACKGROUND

The present invention refers to a portable pump for infusing liquid substances into the body of a living being, particularly for infusing drugs into the body of a human being. The invention further relates to a reservoir for use in the pump, particularly an interchangeable reservoir adapted to contain a drug to be infused through the pump.

As known, the infusion of drugs in liquid form into the body of a living being such as a human being or an animal, can be effected by using electromechanical devices also known as drug infusion pumps. Such pumps can be hospital-type pumps, i.e. intended for stationary use, or they can be portable-type pumps, i.e. intended for being worn by human beings, for instance with the aid of a pouch attached to the body by means of a strap or the like. Portable-type pumps, for obvious reasons, have light weight and require a small amount of space and they further have to meet special requirements, mainly determined by their use conditions, which may vary even widely from one user to another. In this respect, one should consider that portable pumps for drug infusion are usually worn throughout the day and therefore during all the activities typically carried out by a living being, including for instance those related to personal care. Water-tightness, or at least the capacity to operate also in humid environments, for instance in the presence of mist or vapor, is therefore one of the requirements to be preferably met by a portable pump. For this reason, portable-type pumps usually comprise a casing as watertight as possible, which houses the mechanical members and the electric and electronic circuitry controlling operation of the pump and, in some kinds of pumps, also the interchangeable reservoir from which the drug is delivered. An opening provided in the casing allows the passage of a duct through which the drug exiting the reservoir by effect of the thrust imparted by the mechanical members is supplied to the living being's body.

WO 2004/084976 A1 describes an example of a portable pump of the aforementioned type comprising a casing in which a housing is defined for a drug-charged interchangeable vial, said housing having an aperture for inserting the vial and a threaded ferrule which is screwed on a threaded appendix of the casing in order to firmly lock the vial in the housing. The threaded ferrule has a hole for the passage of the duct through which the drug is delivered.

In other types of pumps, the reservoir is located outside the casing containing the pump organs and is attached to the casing by means of mechanical connections of various kinds, which, however, makes it less feasible to obtain a watertight configuration of the pump. EP 1078643 describes a further example of a portable device for drug infusion of this second known type.

The described portable pumps of the first known type, though guaranteeing good humidity-tightness, are not easy to handle, especially by patients who have difficulties in coordinating movements of their hands, as they require insertion of the reservoir in its correct position into the corresponding housing and locking of the reservoir by means of a separate ferrule to be screwed or in case fitted onto the casing. Furthermore, the reservoir, when filled and inserted in its housing provided in the pump, is usually already connected to the cannula for outflow of the drug to the patient and in this case it is obvious that in order to place the ferrule and insert it and screw it onto the pump it will be necessary to temporarily disconnect the cannula from the reservoir, in order to let it pass through the ferrule, with the risk of jeopardizing the sterility of the duct once the duct is connected to the reservoir again. In addition, the ferrule is often difficult to be inserted and screwed and can get lost easily, with consequent impossibility to proceed with the infusion of the drug.

SUMMARY

It is therefore a first object of the invention to provide a pump that overcomes the drawbacks found in prior art pumps and solves the problem of how to make it easy and feasible to insert the interchangeable reservoir while eliminating the risk of loss of sterility in the drug outflow cannula.

It is a further object of the invention to provide a pump of the aforementioned type which can be worn also in humidity-rich environments, under the shower, at the swimming pool and in similar conditions, and is therefore substantially watertight for use in such conditions.

A not least object of the invention is to provide an infusion pump of the portable type that can be manufactured in a cost convenient way and is therefore suitable for large-scale industrial production.

The aforementioned and other objects are achieved with the pump according to the invention and related reservoir, as claimed in the appended claims.

According to a first aspect of a preferred embodiment of the invention, a first advantage is the possibility to insert the reservoir into the pump without having to disconnect the drug outflow cannula from the reservoir.

According to another aspect of a preferred embodiment of the invention, a corresponding advantage results from the providing of a seal ring arranged in the proximity of the opening through which the reservoir is inserted into the pump, thus obtaining a tight seal between the casing wall and the reservoir and preventing humidity penetration into the casing.

According to a further aspect of a preferred embodiment of the invention, a further advantage results from the possibility to insert the reservoir into the pump with a simple double movement, typical of bayonet inserts, of axial approach and rotation by acting on the top of the reservoir, preferably provided with a surface which facilitates grip with the fingers.

According to a particular aspect of the invention the pump, when housing the reservoir, will advantageously result tightly sealed and therefore usable also in humid environments or under the shower or even submersed in a bath tub.

BRIEF DESCRIPTION OF THE DRAWINGS

Some preferred embodiments of the invention will be given merely by way of non-limiting examples with reference to the annexed drawings, in which.

DETAILED DESCRIPTION

Figure 1:
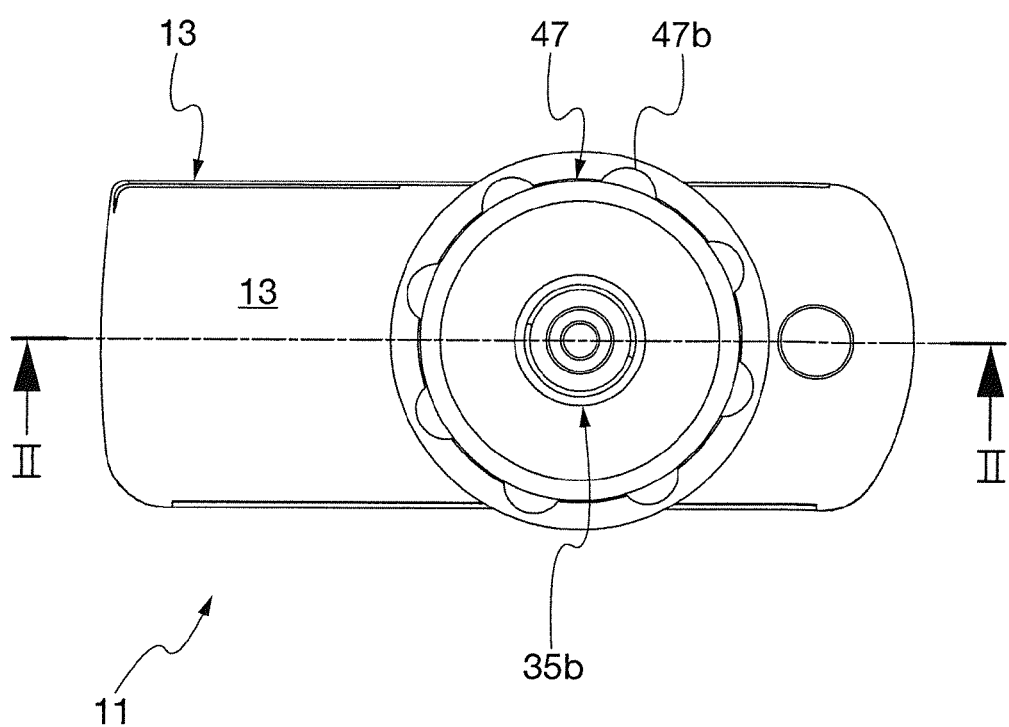
FIG. 1 is a front plan view of the pump of the invention.
Figure 2:
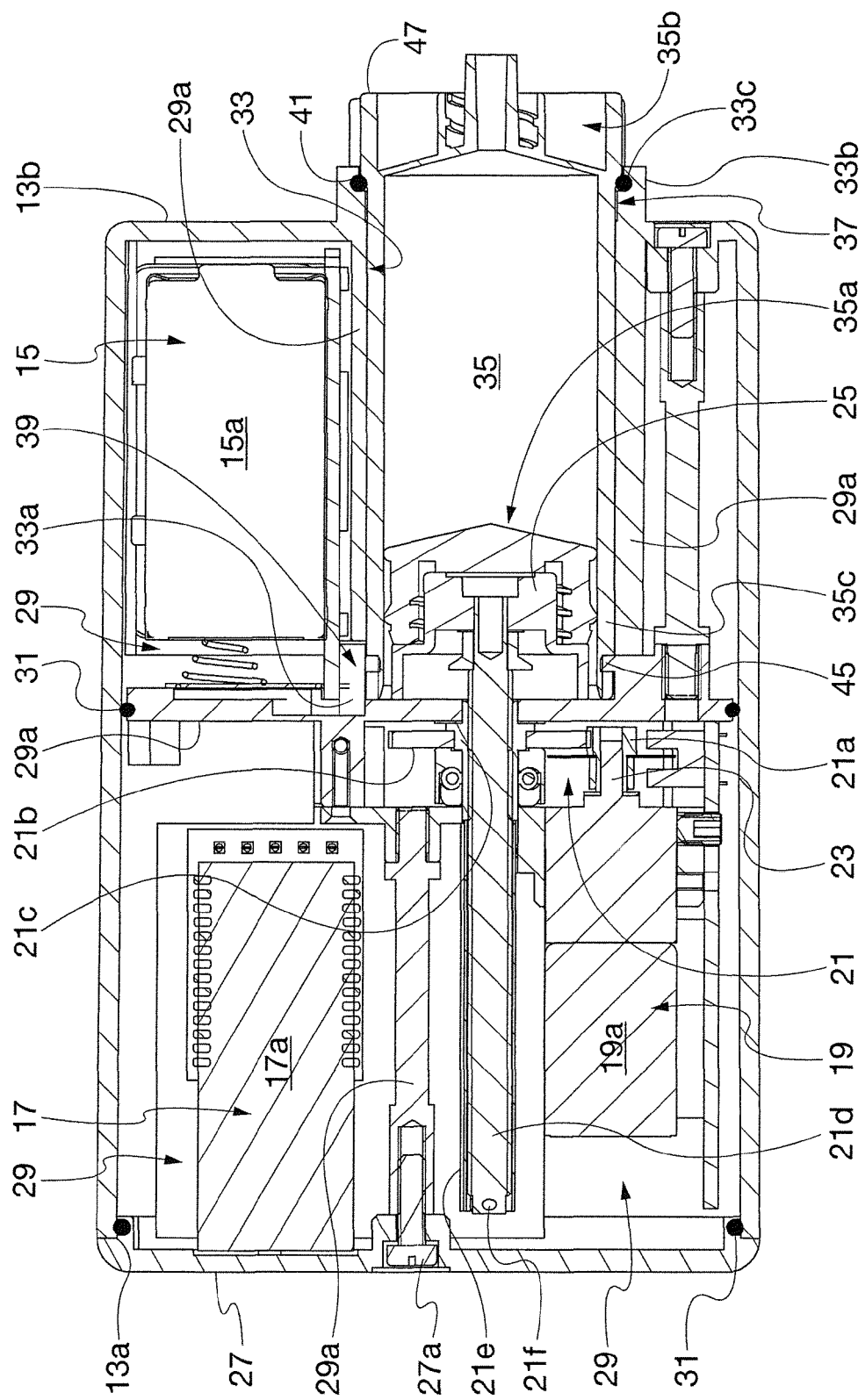
FIG. 2 is a cross-sectional view taken along the line II-II of FIG. 1.
Figure 3:
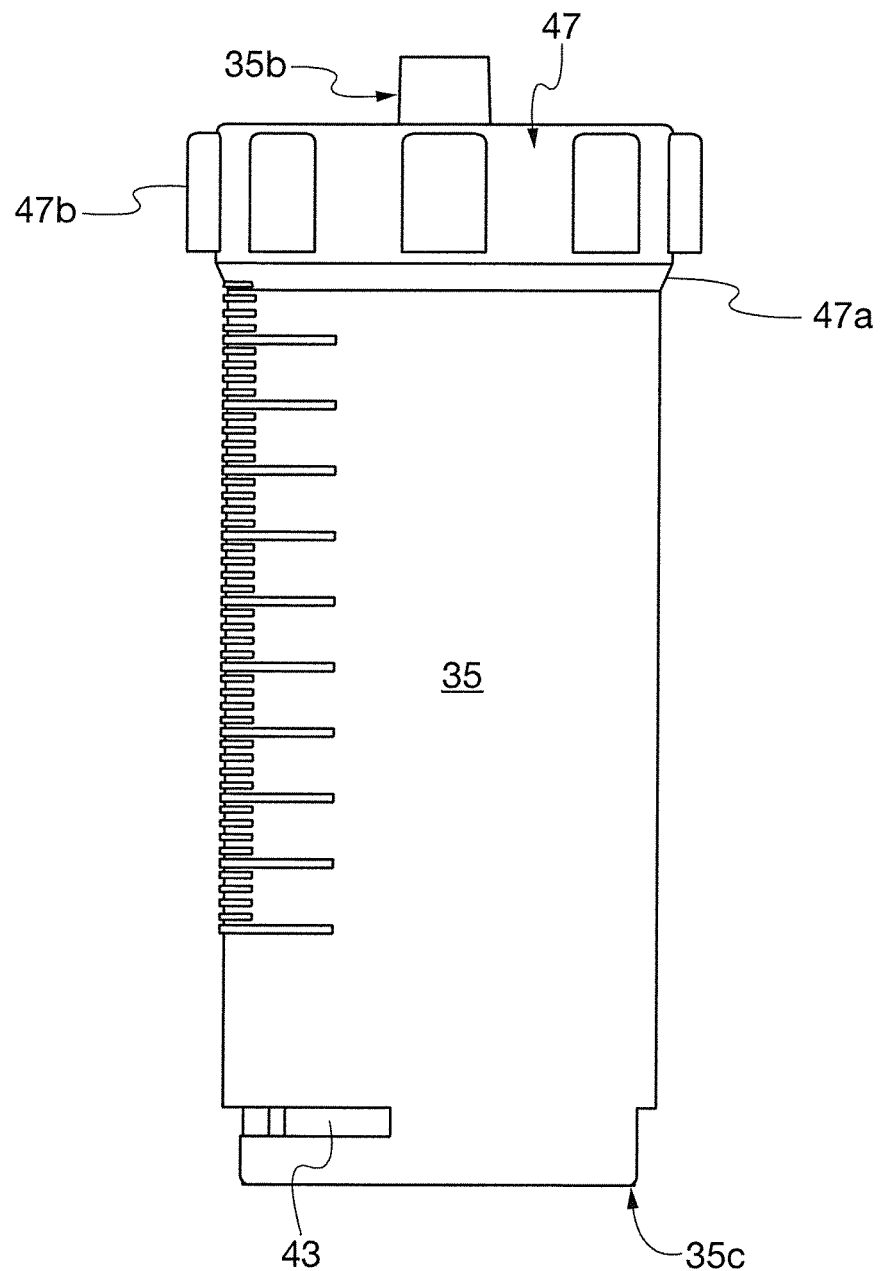
FIG. 3 is a side view of the reservoir.
Figure 4:
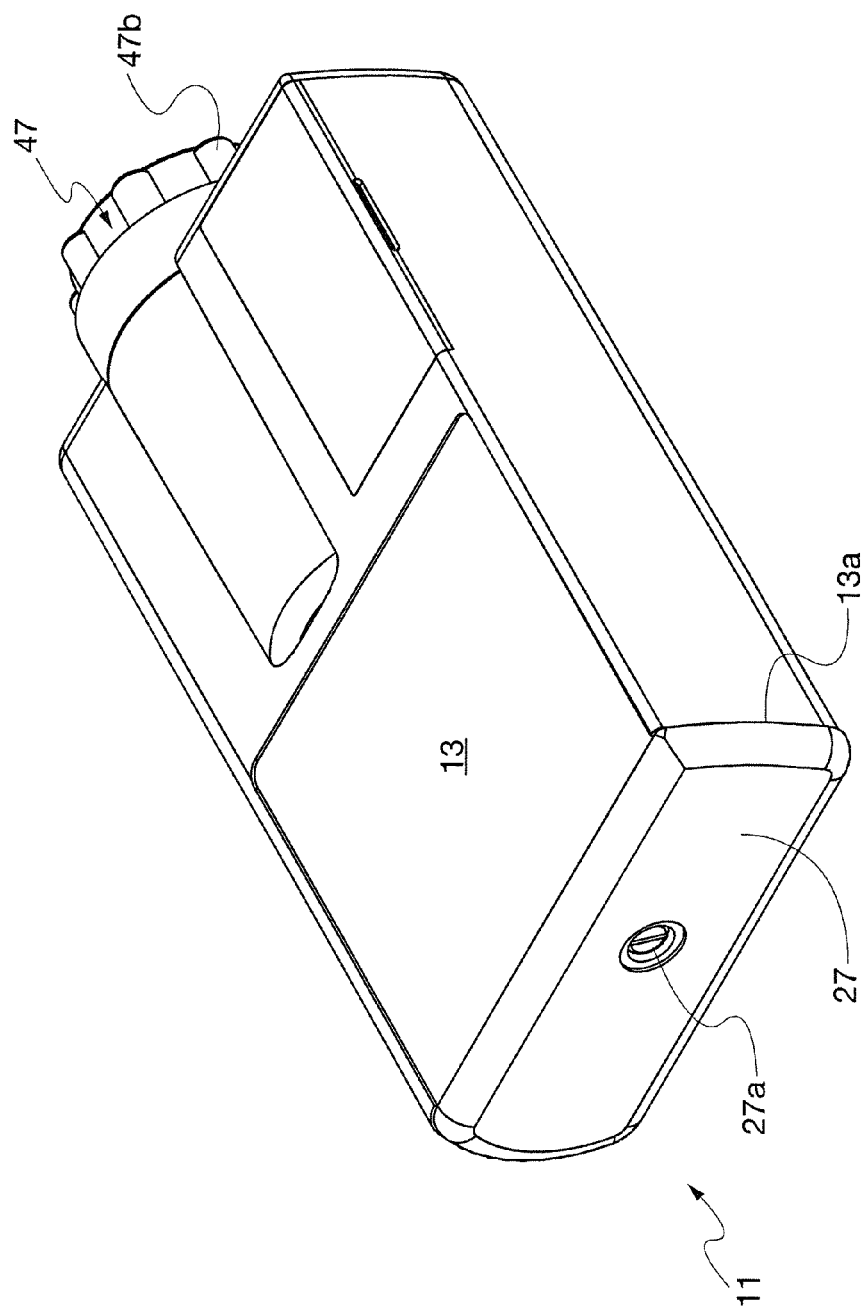
FIG. 4 is a rear perspective view of the pump of FIG. 1.

With reference to the annexed figures, the pump object of the invention, which has been indicated as a whole by reference numeral 11, comprises a casing 13 in which the members that coordinate the operation of the pump are received, as disclosed in more detail in the following description.

In particular, the electromechanical members comprising a power supply unit 15, an electronic control unit 17, an electric motor 19 and an assembly 21 for converting the rotary motion of an output shaft 23 of the motor 19 into a linear sliding motion of an axially movable pusher 25 are received inside the casing 13.

In the embodiment shown, the power supply unit 15 comprises a battery 15a, the electronic control unit 17 comprises an integrated circuit 17a and the electric motor 19 comprises a coreless-type motor 19a. Moreover, still with reference to the embodiment shown, the motion conversion assembly 21 comprises a pair of mutually engaged toothed wheels 21a, 21b, of which one 21a is fixed to the output shaft 23 of the motor 19 and the other one 21b is fixed to a rotatable worm nut 21c supported by a thrust bearing and internally threaded and engaged on an outwardly threaded rod 21d sliding axially inside a linear guide 21e. The guide 21e is further associated to the assembly 21 so as to be fixed relative to the casing 13, whereas the rod 21d is prevented from rotating relative to the guide 21 by means of a radial peg 21f slideable in longitudinal grooves formed within the guide 21e. The rotation of the output shaft 23 causes the rotation of the first toothed wheel 21a which in turn transmits the movement to the second toothed wheel 21b. The worm nut 21c rotates as a consequence of the rotation of the second toothed wheel 21b on the threaded rod 21d and causes axial sliding thereof relative to the guide 21e, owing to the cooperation between the threadings of the worm nut 21c and of the rod 21d. In other embodiments it will be possible to provide different units and mechanisms for moving the pusher 25.

Preferably the casing 13 comprises a parallelepipedal box-like body and has an open base 13a provided with a lid 27 closed by means of a screw 27a which engages the body of the housing 13. Inside the casing 13 there are preferably defined compartments 29 which are delimited by partition walls 29a and/or stiffening tie-rods and house the components of the pump 11. Sealing gaskets 31 are also preferably provided between the lid 27 and the body of the casing 13, at the base 13a, in order to guarantee water-tightness of the casing 13, and preferably also inside the casing 13, between the partition walls 29a and the walls of the casing 13, when said partition walls are made as removable from the casing 13, thus ensuring water-tightness of the compartments 29 one with respect to the other and higher protection against damages resulting from humidity penetration into the casing.

Inside the casing 13, in case inside one of the compartments 29 if any, a housing 33 is provided for an interchangeable reservoir 35 containing the liquid to be delivered though the pump 11. The housing 33 further comprises an opening 37 through which the housing 33 is in communication with the outside of the casing 13, for inserting the reservoir 35 into the housing 33. In the embodiment shown, the opening 37 is provided in the base 13b of the casing 13 opposite to the open base 13a. The opening 37 also has a cross-section with the same shape as the reservoir 35, whereby, in the most frequent case in which the reservoir 35 has a circular cross-section, the opening 37 will also have a circular cross-section, typical of a drug infusion reservoir in the form of a syringe. The size of the opening 37 will further be such as to allow the passage of the reservoir 35 with press fit so as to guarantee the necessary hydraulic seal and prevent radial movements of the reservoir 35.

The head of the slideable rod 21d is equipped with a pusher 25, which is of a cap-like form in the embodiment shown, capable of causing the displacement of a plunger 35a slideable inside the interchangeable reservoir 35 in which the substance to be infused through the pump is contained. In the absence of the reservoir 35 the pusher 25 is free to axially slide inside the housing 33, whereas in the presence of the reservoir 35 the pusher 25, during advancement of the rod 21d, comes into abutment against the plunger 35a and causes the outflow of the liquid containing in the reservoir 35 through a bored appendix 35b of the reservoir 35 which is on the opposite side with respect to the reservoir open base 35c from which the pusher 25 enters. The appendix 35b, axially bored for letting out the substance to be infused, protrudes from the opening 37 when the reservoir 35 is accommodated in the housing 33.

According to the invention the housing 33 for the interchangeable reservoir 35 includes, with respect to the opening 37, a distal portion 33a provided with mechanical means for reversible engagement 39 for corresponding means provided in the base of the reservoir 35, opposite to the appendix 35b, and a proximal portion 33b provided with an annular sealing gasket 41 which surrounds the reservoir 35 and forms a tight seal between the reservoir 35 and the casing 13 wall, when the reservoir 35 is mechanically engaged within the housing 33 through said engagement means 39.

Advantageously, thanks to this arrangement, when the reservoir 35 is mechanically secured within the housing 33 through the engagement means 39, the tight seal between the reservoir 35 and the casing 13 wall is simultaneously guaranteed by the annular gasket 41.

The reservoir 35 comprises a hollow cylindrical body which is open at its end or base 35c opposite to the appendix 35b and is provided, at its open end 35c, with mechanical means for reversible engagement comprising radial seats 43 accessible from the outside of the reservoir 35 for the engagement of corresponding radial protrusions 45 formed in said engagement means 39 at the bottom of the housing 33. However, it will be possible to provide also a reverse arrangement, i.e. in which the seats are formed in the casing body and the protrusions are formed on the reservoir body. A bayonet insert is thus provided, which usually involves rotation by an arc smaller than 90° of the reservoir relative to the pump. Alternatively, a threaded insert can be provided, which, however, will usually involve the need to rotate the reservoir by an arc bigger than 90°.

Next to the appendix 35b the reservoir 35 preferably comprises a ferrule 47 radially protruding from the body of the reservoir 35 and thus defining an annular perimeter 47a for abutment of the sealing gasket 41. The ferrule 47 preferably further comprises radial projections 47b for enabling an operator to grip the reservoir 35 with his/her fingers when it is to be inserted into or taken out of the housing 33 with an axial movement and rotate it once it has reached, with its open base 35c, the bottom of the housing 33, for engaging the mechanical means 39 provided therein into the body of the reservoir 35.

According to a preferred embodiment of the invention, the body of the reservoir 35 is made of plastics, for instance with the molding technique, and the ferrule 47 is integral with said body, the ferrule being preferably made as a single piece with the body or glued to the body.

The appendix 35b is preferably provided with a coupling part of the "luer lock" type for allowing to insert the cannula of an outflow tubing or other device for the outflow of the substance delivered by the pump 11 towards the body of the living being.

According to a preferred embodiment of the invention, the gasket 41 is an O-ring made of natural or synthetic rubber. Furthermore, still according to a preferred embodiment of the invention, the proximal portion 33b of the housing 33 comprises an annual groove 33c receiving said ring 41.

The pump and reservoir as described and illustrated are susceptible to numerous variants and modifications falling within the same inventive principle.

The invention claimed is:

1. A portable pump (11) for infusing liquid substances into the body of a living being, said pump being provided with a casing (13) which receives electromechanical members comprising a power supply unit (15), an electronic control unit (17), an electric motor (19), an assembly (21) for converting the rotary motion of an output shaft (23) of the motor (19) into a linear sliding motion of a pusher (25) axially moveable for causing the movement of a plunger (35a) slideable within an interchangeable reservoir (35), open at one end (35c) thereof, in which the substance to be infused through the pump is contained and which is accommodated in a housing (33) inside the casing (13), wherein the housing (33) is in communication with the outside through an opening (37) which is formed in one of the casing walls and through which the reservoir (35) can be inserted into and removed from the housing and from which an appendix (35b) of the reservoir protrudes for the exit of the substance to be infused when the reservoir is accommodated in the housing, wherein the housing for the interchangeable reservoir includes, with respect to the opening (37), a distal portion (33a) provided with mechanical means for reversible engagement (39) for the reservoir end (35c) opposite to the appendix (35b) and a proximal portion (33b) provided with an annular sealing gasket (41) which surrounds the reservoir (35) and foams a tight seal between the reservoir (35) and the casing (13) wall when the reservoir is mechanically engaged within the housing (33) through said engagement means (39), so that when the reservoir (35) is mechanically secured within the housing (33) through the engagement means (39), the tight seal between the reservoir (35) and the casing (13) wall is simultaneously guaranteed and wherein the reservoir (35) comprises a hollow cylindrical body which is open at its end (35c) opposite to the appendix (35b) and is provided, at its open end (35c), with radial seats (43) accessible from the outside of the reservoir (35) for the engagement of corresponding radial protrusions (45) formed in said engagement means (39) at the bottom of the housing (33).

2. The pump according to claim 1, wherein the reservoir (35) comprises a ferrule (47) which is provided with radial projections (47a) and is arranged next to the appendix (35b) and radially protrudes from the reservoir body, said ferrule thus defining an annular perimeter (47a) for abutment of the sealing gasket (41).

3. The pump according to claim 2, wherein the appendix (35b) is provided with a coupling part of a "luer lock" type.

4. The pump according to claim 1, wherein the appendix (35b) is provided with a coupling part of a "luer lock" type.

5. The pump according to claim 1, wherein the casing (13) comprises a box having a parallelepipedal shape with an open base (13a) and provided with a lid (27) and wherein compartments (29) are defined for hosting said units inside the casing (13).

6. The pump according to claim 5, wherein the housing (33) for the reservoir (35) is defined inside the box and the opening (37) is located at the box base opposite to the open base (13a).

7. The pump according to claim 1, wherein the gasket (41) is an O-ring made of natural or synthetic rubber.

8. The pump according to claim 7, wherein the proximal portion (33b) of the housing (33) comprises an annular groove (33c) receiving said O-ring (41).

9. Reservoir (35) for use in a pump for infusing liquid substances into the body of a living being, said pump being provided with a casing (13) which receives electromechanical members comprising a power supply unit (15), an electronic control unit (17), an electric motor (19), an assembly (21) for converting the rotary motion of an output shaft (23) of the motor (19) into a linear sliding motion of a pusher (25) axially moveable for causing the movement of a plunger (35a) slideable within an interchangeable reservoir (35), open at one end (35c) thereof, in which the substance to be infused through the pump is contained and which is accommodated in a housing (33) inside the casing (13), wherein the housing (33) is in communication with the outside through an opening (37) which is formed in one of the casing walls and through which the reservoir (35) can be inserted into and removed from the housing and from which an appendix (35b) of the reservoir protrudes for the exit of the substance to be infused when the reservoir is accommodated in the housing, wherein the housing for the interchangeable reservoir includes, with respect to the opening (37), a distal portion (33a) provided with mechanical means for reversible engagement (39) for the reservoir end (35c) opposite to the appendix (35b) and a proximal portion (33b) provided with an annular sealing gasket (41) which surrounds the reservoir (35) and forms a tight seal between the reservoir (35) and the casing (13) wall when the reservoir is mechanically engaged within the housing (33) through said engagement means (39), so that when the reservoir (35) is mechanically secured within the housing (33) through the engagement means (39), the tight seal between the reservoir (35) and the casing (13) wall is simultaneously guaranteed and wherein the reservoir (35) comprises a hollow cylindrical body which is open at its end (35c) opposite to the appendix (35b) and is provided, at its open end (35c), with radial seats (43) accessible from the outside of the reservoir (35) for the engagement of corresponding radial protrusions (45) formed in said engagement means (39) at the bottom of the housing (33).

10. Reservoir according to claim 9, wherein the reservoir comprises next to said appendix (35b), with a ferrule (47) radially protruding from the reservoir body, said ferrule defining an annular perimeter (47a) for abutment of a sealing gasket (41) provided in the pump.

* * * * *